(12) United States Patent
Yasuda et al.

(10) Patent No.: US 8,028,835 B2
(45) Date of Patent: Oct. 4, 2011

(54) MEDICAL PRODUCTS AND MEDICAL PRODUCT ORDERING SYSTEM

(75) Inventors: Kenichi Yasuda, Shizuoka (JP); Jun Iwami, Shizuoka (JP); Shigeki Numata, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1564 days.

(21) Appl. No.: 11/187,233

(22) Filed: Jul. 22, 2005

(65) Prior Publication Data
US 2006/0016897 A1    Jan. 26, 2006

(30) Foreign Application Priority Data

Jul. 23, 2004   (JP) .................................. 2004-216398

(51) Int. Cl.
B65D 85/00 (2006.01)
A61B 19/02 (2006.01)
G08B 5/22 (2006.01)
(52) U.S. Cl. .................. 206/459.1; 206/438; 340/572.8
(58) Field of Classification Search .................. 206/363, 206/438, 459.5, 459.1; 340/572.8; 235/492
See application file for complete search history.

(56) References Cited

U.S. PATENT DOCUMENTS

| | | | | |
|---|---|---|---|---|
| 4,695,954 A | * | 9/1987 | Rose et al. ...................... | 221/15 |
| 5,852,590 A | * | 12/1998 | de la Huerga ................... | 368/10 |
| 5,982,284 A | * | 11/1999 | Baldwin et al. ............ | 340/572.8 |
| 6,259,369 B1 | | 7/2001 | Monico | |
| 6,259,654 B1 | | 7/2001 | de la Huerga | |
| 6,421,013 B1 | * | 7/2002 | Chung ................... | 343/700 MS |
| 7,294,917 B2 | * | 11/2007 | Matsushita et al. ............ | 257/679 |
| 7,327,266 B2 | * | 2/2008 | Watanabe et al. .......... | 340/572.8 |
| 7,336,270 B2 | * | 2/2008 | Sato .............................. | 345/204 |
| 2001/0028308 A1 | * | 10/2001 | De La Huerga ........... | 340/573.1 |
| 2002/0036237 A1 | * | 3/2002 | Atherton et al. .............. | 235/492 |

(Continued)

FOREIGN PATENT DOCUMENTS

JP        11-011536        1/1999
(Continued)

OTHER PUBLICATIONS

European Search Report for EP 05 01 5765, dated Nov. 14, 2005.

(Continued)

*Primary Examiner* — J. Gregory Pickett
*Assistant Examiner* — Ernesto Grano
(74) *Attorney, Agent, or Firm* — Buchanan Ingersoll & Rooney PC

(57) ABSTRACT

A transaction management system is capable of simply and accurately gathering information about the use of medical products with minimized human errors and automatically executing issuance of invoices of suppliers and restocking of used products on the basis of the results of use of products deposited at medical centers. The system comprises a computer system having an antenna electrically connected to a reader and a medical product encapsulated in a sterilized environment in a package. The package is provided with an IC tag arranged such that signal transmission and/or reception is disabled while the package remains unopened so that the medical product is in the sterilized condition. The IC tag becomes wirelessly communicable with the antenna when the package is opened to remove the medical product. The computer system reads the product information about the medical product from the IC tag now wirelessly communicable with the antenna and, on the basis of the obtained product information, places an order to a supplier for the replenishment of the used medical product through a dedicated line or an external network.

11 Claims, 9 Drawing Sheets

U.S. PATENT DOCUMENTS

| | | | |
|---|---|---|---|
| 2002/0067267 A1 | 6/2002 | Kirkham | |
| 2002/0188259 A1 | 12/2002 | Hickle et al. | |
| 2002/0190364 A1* | 12/2002 | Dobashi et al. | 257/679 |
| 2004/0008123 A1 | 1/2004 | Carrender et al. | |
| 2004/0026519 A1* | 2/2004 | Usami et al. | 235/492 |
| 2005/0011960 A1* | 1/2005 | Koike et al. | 235/492 |
| 2006/0170551 A1* | 8/2006 | Nakamura et al. | 340/572.1 |

FOREIGN PATENT DOCUMENTS

| | | |
|---|---|---|
| JP | 2001-136671 | 3/2001 |
| JP | 2002-119577 | 4/2002 |
| JP | 2002-179223 | 6/2002 |
| JP | 2003-16198 | 1/2003 |
| JP | 2003-132145 | 5/2003 |
| JP | 2003-276809 | 10/2003 |
| JP | U2003-270315 | 4/2004 |
| WO | 03/090663 A1 | 11/2003 |

OTHER PUBLICATIONS

European Search Report issued on Jun. 25, 2010 by European Patent Office in corresponding European Application No. 08154299.5.

* cited by examiner

EXAMPLE OF SYSTEM CONFIGURATION

EXAMPLE OF DISPLAY

EXAMPLE OF TERMINAL DEVICE PROCESSING IN MEDICAL CENTER

EXAMPLE OF HOST PROCESSING

MEDICAL PRODUCTS AND MEDICAL PRODUCT ORDERING SYSTEM

This application is based on and claims priority under 35 U.S.C. §119 with respect to Japanese Application No. 2004-216398 filed on Jul. 23, 2004, the entire content of which is incorporated herein by reference.

FIELD OF THE INVENTION

The present invention generally relates to an order acceptance and placement system and to medical products for use in such system. More particularly, the invention pertains to an order acceptance and placement system for accurately comprehending and recording medical products used for particular medical procedures and automatically carrying out transactions between medical product vendors and medical centers on the basis of the information that occurs when such packaged sterilizing products as medical instruments, drugs and medicines, and medical support products are unpackaged (or used).

BACKGROUND OF THE INVENTION

Methods have been proposed in which medical equipment is managed in medical centers by use of, for example, barcodes and IC tags.

For example, a medical management system is described in Japanese Patent Laid-open No. 2003-16198 in which barcodes are directly attached to the equipment for use in medical centers and the packs storing the equipment. This system requires the reading of barcodes by bringing an optical reader called a barcode reader close to each barcode, thereby manually reading information stored in each barcode.

Another surgical products management system is described in Japanese Patent Laid-open No. 2002-179223 in which surgical products each attached with an IC tag are put on a cart, and the cart is passed through a reading gate before and after each surgical operation to gather the information about products used (or taken off from the cart) in each surgical operation. Although this system does not require the manual operation of the card reader, it is necessary with this system to pass each cart loaded with surgery products through a dedicated gate before and after each surgical operation to identify the surgical products used in a particular surgical operation on the basis of the difference in product information before and after the operation.

On the other hand, systems supporting transactions between medical centers and medical products sales companies by use of barcodes and IC tags are disclosed in Japanese Patent Laid-open No. 2002-119577. The system described in Japanese Patent Laid-open No. 2002-119577 is associated with a system for managing medical products such as catheters, in which repository entering/dispatching management is executed through a storage having a door connected to a computer via a scanner with an antenna arranged inside. In this system, when products are entered in the repository, products information is manually entered through an input device and control labels based on ID tag are attached to products. When products have been dispatched from the repository with radio waves transmitted by closing the door, the ID tag information of the products left in the repository is gathered to be matched with the repository entry information, thereby obtaining repository dispatching information. On the basis of the obtained repository dispatching information, order placing information is automatically transmitted to suppliers.

SUMMARY

According to one aspect, a medical product storage pack comprises a package, a medical product encapsulated in a sterilized environment in the package, and an IC tag arranged at the package such that at least one of signal transmission and signal reception by the IC tag is disabled, and such that at least one of signal reception and signal transmission by the IC tag is enabled upon opening the package to permit removal of the medical product from the package.

According to another aspect, a medical product storage pack comprises a closed package possessing an enclosed space in which is located a medical product under sterilized conditions, with the closed package being openable so that the space is no longer under sterilized conditions to permit removal of the medical product from the package. An IC tag is arranged at the package. In addition, the medical product storage pack comprises means for disabling at least one of signal transmission and signal reception by the IC tag when the package is closed and for enabling at least one of the signal reception and the signal transmission by the IC tag when the package is opened so that the space is no longer under sterilized conditions.

According to an additional aspect, a medical product order accepting and placing system comprises a computer system electrically connected to a first antenna by way of a reader device and a medical product encapsulated in a sterilized environment in a package. The package is provided with an IC tag arranged at the package such that at least one of signal transmission and signal reception by the IC tag is disabled and such that at least one of signal reception and signal transmission by the IC tag is enabled upon opening the package to permit removal of the medical product from the package. The computer system comprises a storage section in which is stored product information about the medical product obtained from a signal received by the first antenna from the enabled IC tag, and order placing means for placing an order to a supplier of the medical product through at least one of a dedicated line and an external network based on the product information stored in the storage section.

According to a further aspect, a method comprises receiving data from an enabled IC tag provided at a package possessing an enclosed space in which is located a medical product under sterilized conditions, with the IC tag being provided at the package such that the IC tag is disabled from at least one of signal transmission and signal reception when the medical product is in the enclosed space under sterilized conditions and such that the IC tag is enabled for at least one of the signal reception and the signal transmission when the package is opened so that the enclosed space is no longer under sterilized conditions to permit the medical product to be removed from the package. The method also involves storing, in a storage section of a computer, product information about the medical product obtained from the signal received by an antenna from the enabled IC tag.

BRIEF DESCRIPTION OF THE DRAWING FIGURES

DETAILED DESCRIPTION

It should be noted that the present embodiment, applied to medical products for use in medical centers, is a system for executing order placement/acceptance of medical products for use in medical centers, with the medical products being stored in a sterilized state.

Figure 1:
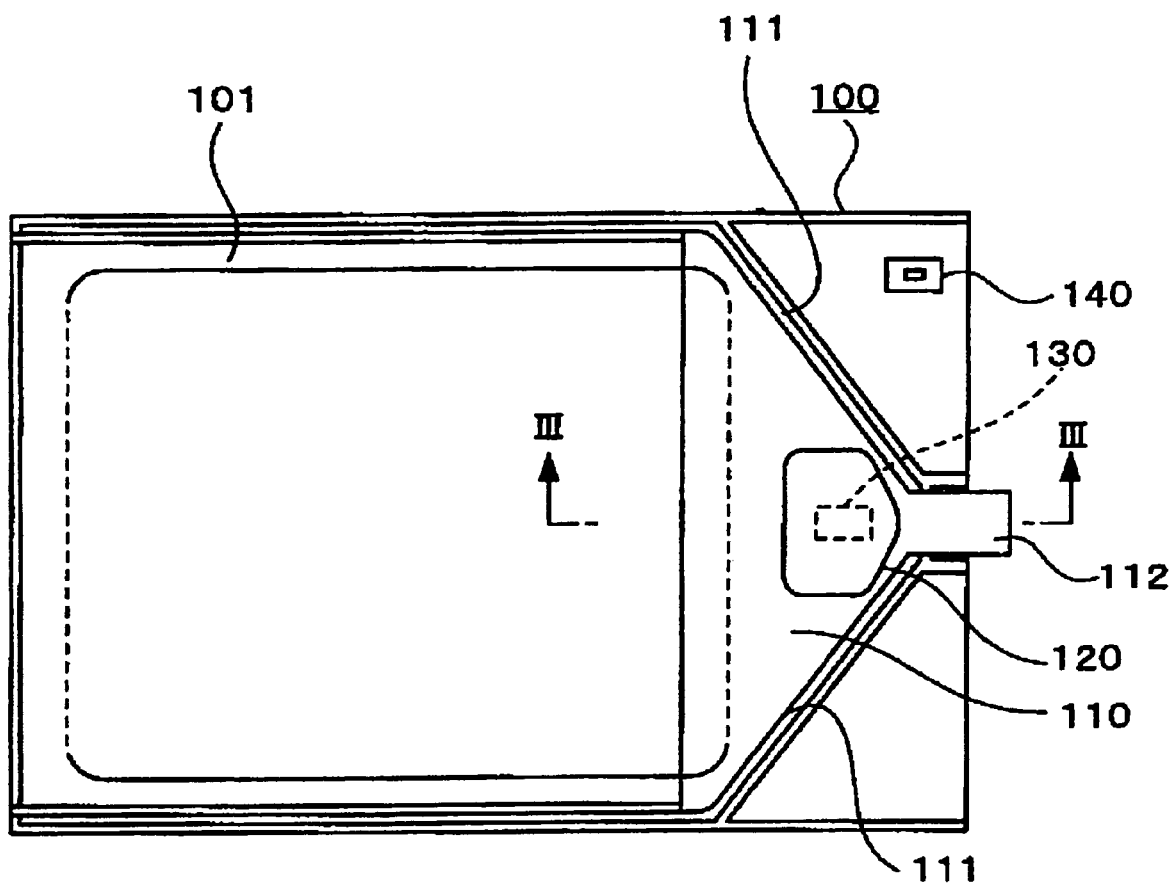
FIG. 1 is a top view illustrating an example of a medical product practiced as one embodiment of the invention.

First, a configuration of a medical product storage pack according to one embodiment will be described with reference to FIGS. 1-4. FIG. 1 illustrates an example of a configuration of a medical product storage pack 100 constituting the medical product according to one embodiment of the invention. The medical product storage pack 100 comprises a package having a storage section 101 for accommodating a medical product(s) or medical goods so that the medical product is stored in a sterilized state or sterilized environment within the package. More specifically, as shown in the cross-sectional view of FIG. 3, the storage section 101 is made up of a transparent synthetic resin sheet 102 and a gas-permeable sheet 103. As shown in FIG. 1, these sheets are tightly attached to each other along the peripheries of the sheets, with a space formed by these sheets providing the storage section 101. By way of example, the gas-permeable sheet 103 is made of nonwoven fabric.

Medical products that can be accommodated in the storage section 101 include, for example, a catheter adapted to be introduced into the human body, especially a blood vessel, and attachments for the catheter. Such medical products must be in a sterilized condition. Normally, these medical products are used in a disposable manner and are sold in sterilized sealed packs. Therefore, once the sterilization ceases to be in effect by unpackaging, these medical products must be discarded even if they are not actually used. Consequently, these products may be handled on a basis in which "unpackaging" is equivalent to "used".

The gas-permeable sheet 103 has a property of transmitting gases but not bacteria and the like. Use of the gas-permeable sheet 103 allows the use of ethylene oxide gas for sterilization. It should be noted that if sterilization is made not by gases but by gamma rays or electron beam, sealed packaging without the use of gas-permeable sheets may be used.

Figure 2:
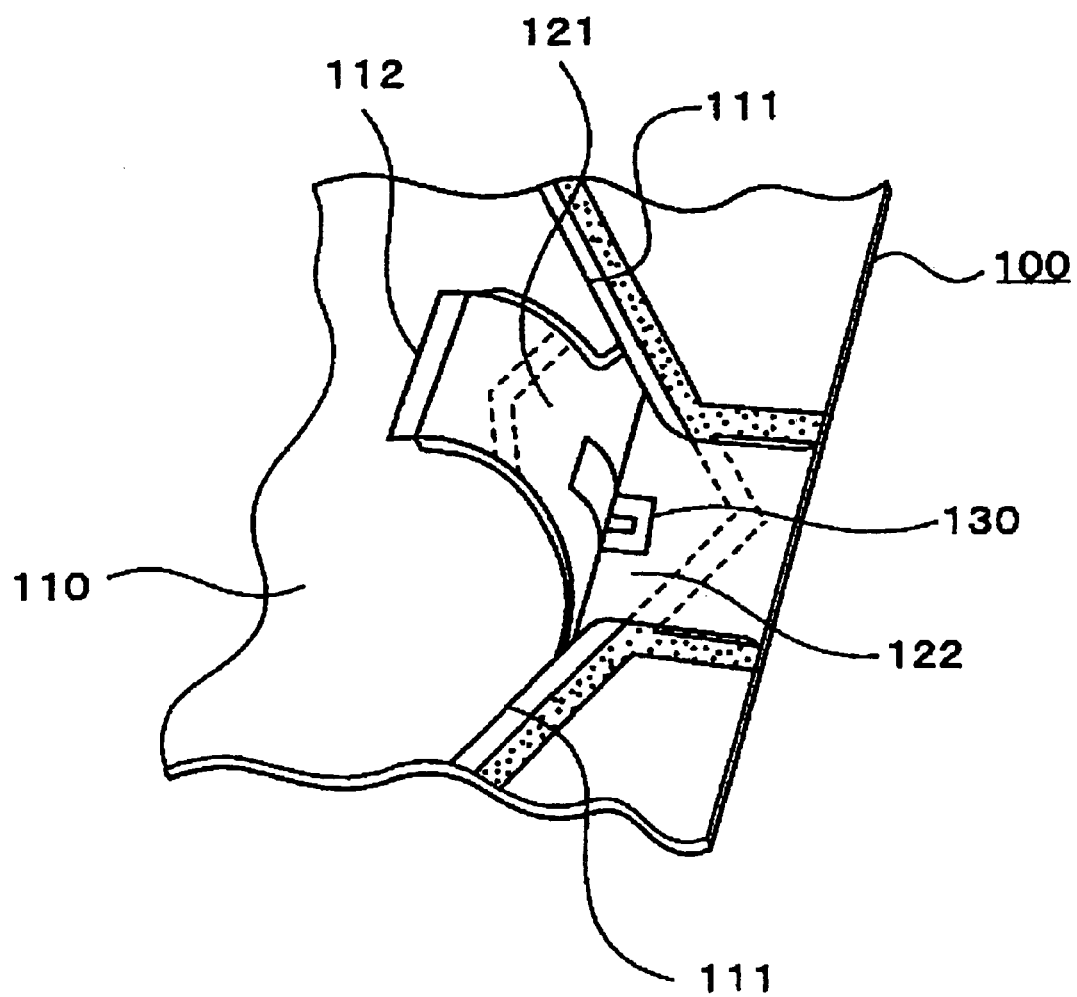
FIG. 2 is an enlarged partial sectional view illustrating a part of the medical product shown in FIG. 1 in an unpackaged state.
Figure 3:
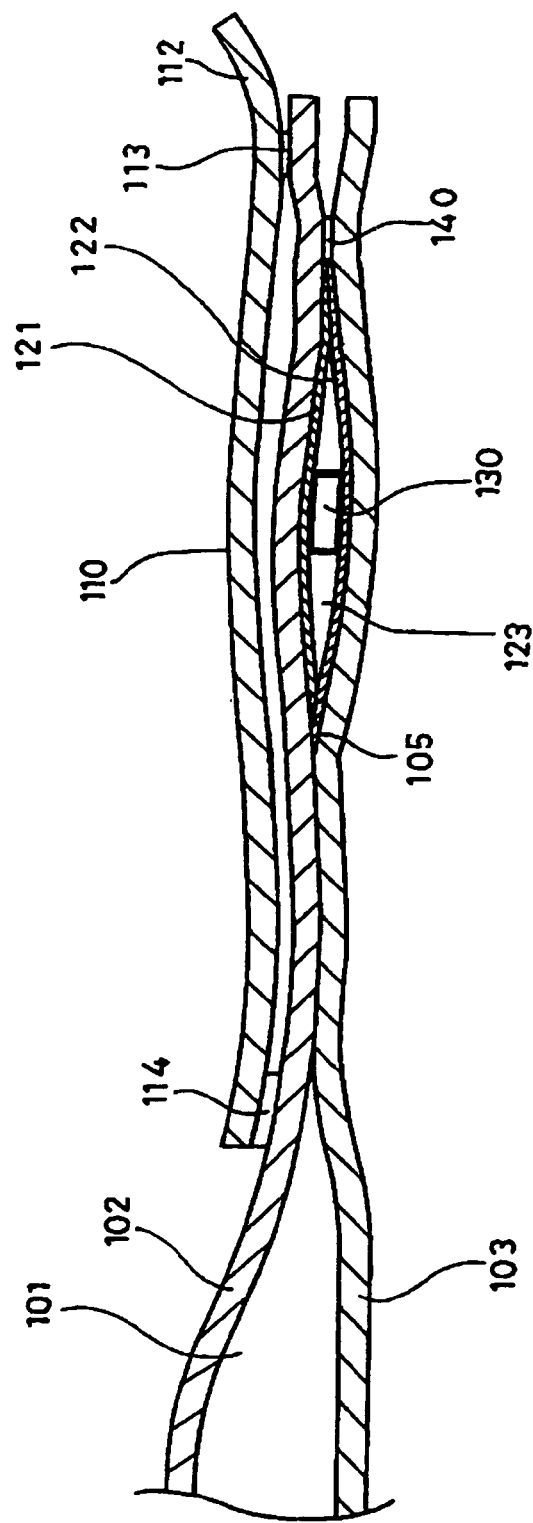
FIG. 3 is a cross-sectional view of the medical product shown in FIG. 1 taken along the section line III-III in FIG. 1.
Figure 4:
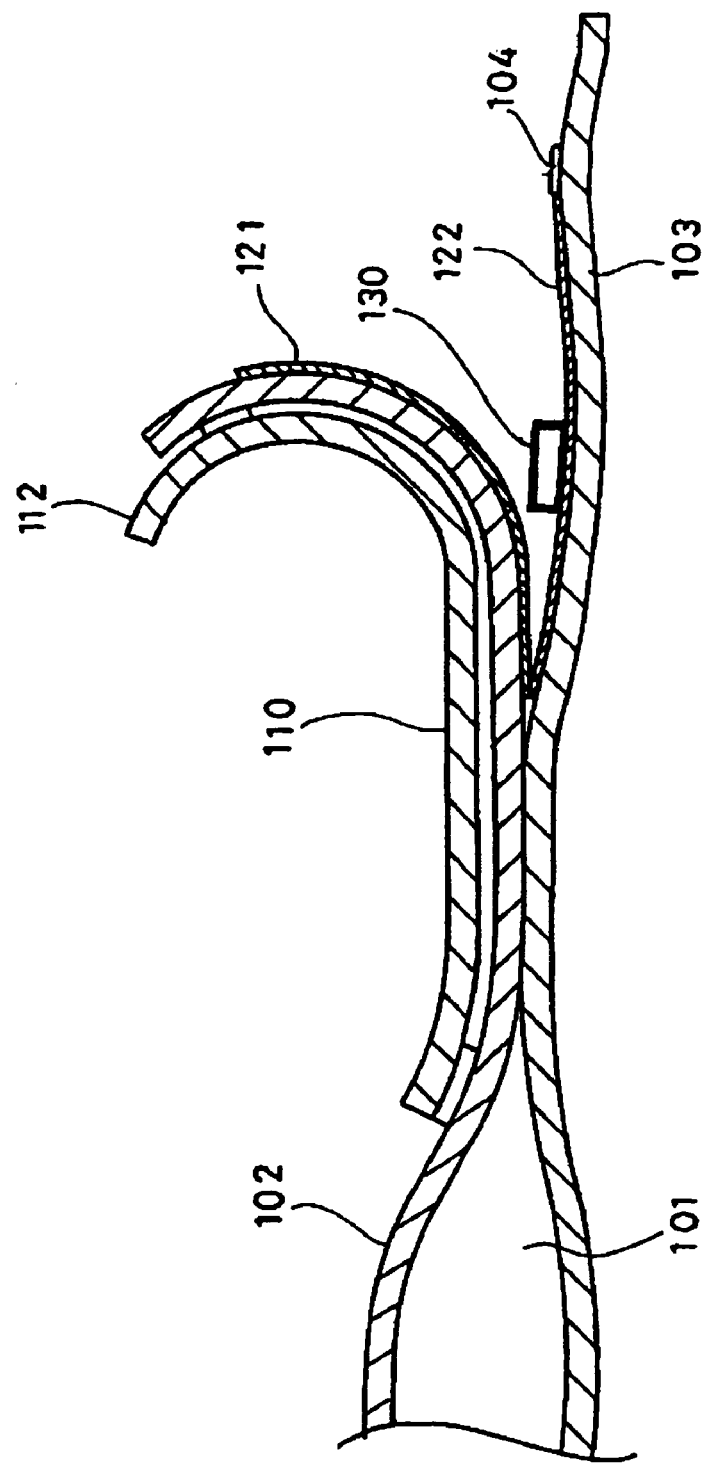
FIG. 4 is a cross-sectional view of the medical product shown in FIG. 1 taken along the section line III-III shown in FIG. 1 in an unpackaged state.

The medical product storage pack 100 is constructed such that it is unpackaged or opened by tearing off the synthetic resin sheet 102. That is, as shown in FIGS. 1 and 3, the synthetic resin sheet 102 extends along the length (to the right end shown in FIG. 1) of the rectangular pack and an unpacking sheet 110 is attached to the top side of the extended portion of the synthetic resin sheet 102. The unpacking sheet 110 is made of a sheet material higher in strength than the material of the synthetic resin sheet 102. One end of the unpacking sheet 110 projects to or terminates at a pull section 112. The pull section 112 can be grasped or held by a user to pull the unpacking sheet 110 and peel off the unpacking sheet 110 along peel-off lines 111 forming a V-shaped peel-off section. The peel-off lines 111 are defined by a reinforcement member such as an adhesive tape attached to the transparent synthetic resin sheet 102. Therefore, as shown in FIG. 2 for example, pulling the pull section 112 in the direction toward the other end rips the synthetic resin sheet 102 on the surface of the medical product storage pack 100 in a V-shape, thereby exposing the medical product accommodated in the storage section 101 and making the medical product ready to be taken out. FIG. 4 shows a state similar to FIG. 3, except with the unpacking sheet 110 peeled back along the lines 111 at the time of unpackaging.

In this embodiment, an IC (integrated circuit) tag is attached to a portion of the medical product storage pack 100 which extends from (i.e., is located to the side of) the storage section 101 of the medical product storage pack 100. The data stored in an IC chip embedded in the IC tag may be read when the IC tag is positioned in the vicinity of an IC tag reading antenna to be described later, by means of wireless communication. In some cases, data may be stored in the IC chip by wireless communication. The IC tag is configured by arranging the IC chip and the antenna on a small-area base, for example. Generally, the IC tag is adapted to operate by electric power that is caused by the reception of a radio wave from the IC tag reading antenna. Alternatively, the IC tag itself may incorporate a battery.

In this illustrated embodiment, two IC tags are arranged on the medical product storage pack 100 as shown in FIG. 1. The IC tags include a first IC tag 130 and a second IC tag 140. The IC tag stores product information such as the name of the product, the model designation, the sterilization lot number, the seller, the manufacturer, the medical center name and/or a product unique ID number (serial number). The two IC tags 130, 140 may both store these pieces of data; however, at least one (the IC tag 140, for example) of these IC tags stores the data for identifying the other IC tag. Alternatively, the first IC tag 130 may only store limited data such as its serial number and the data for identifying this IC tag.

The first IC tag 130 is arranged such that, unless the medical product storage pack 100 is unpackaged or opened, the first IC tag 130 cannot wirelessly communicate with an external antenna. The second IC tag 140 is arranged such that the second IC tag 140 may wirelessly communicate with an external antenna if the medical product storage pack 100 is kept packaged or unopened.

More specifically, the first IC tag 130 is arranged between the synthetic resin sheet 102 that is peeled off at the time of unpackaging and the gas-permeable sheet 103 as shown in FIG. 2. In this case, the arrangement of the first IC tag 130 is at a position away from the storage section 101, namely, in a space 123 between a shield film 121 on the side of the synthetic resin sheet 102 and a shield film 122 on the side of the gas-permeable sheet 103.

The shield film 121 and the shield film 122 function as electromagnetic interference sealed members. By way of example, these shield films may be formed by applying an electrically conductive coating compound to a packaging material made of resin. This coating compound is made of metal powders such as copper, silver, or nickel, a binder such as resin, and a solvent. In order to attain a high conductivity, at least 10 to 15% by weight of the metal powders is included.

The first IC tag 130 is arranged at a position covered with the shield film 121 and the shield film 122 as described above, thereby blocking the wireless communication between the external antenna and the antenna of the first IC tag 130 side by the shield film 121 and the shield film 122. In this way, the first IC tag 130 cannot be recognized when the medical product storage pack 100 is in a packaged state.

When the medical product storage pack 100 is unpackaged or opened, the synthetic resin sheet 102 is peeled off with the unpacking sheet 110 as shown in FIGS. 2 and 4 and the shield film 121 is removed to clear the shielding, upon which the first IC tag 130 is ready to wirelessly communicate with the outside. Namely, as shown in FIG. 2, first, pulling the pull section 112 toward the other end pushes up or lifts the upper shield film 121 to expose the first IC tag 130 to the atmosphere or air. Next, the storage section 101 in which a medical product is sealed is unpackaged.

In the above description, a resin sheet applied with an electrically conductive coating compound is attached to the inside of the synthetic resin sheet 102 and the gas-permeable sheet 103. Alternatively, the electrically conductive coating compound may be applied directly to a portion inside the synthetic resin sheet 102 to which the tag is attached, thereby making the portion function as an electromagnetic shield member. Still alternatively, the above-mentioned electrically conductive coating compound may be mixed in the resin sheet for packaging beforehand. Yet alternatively, the electromagnetic shield material may be formed in a laminated manner by encapsulating etched aluminum foil or a metal mesh for example in the resin.

The second IC tag 140 is arranged so as to be able to wirelessly communicate with the outside antenna if the medical product storage pack 100 is not unpackaged. By way of example, the second IC tag 140 can be attached to the synthetic resin sheet 102 as shown in FIG. 1.

Figure 5:
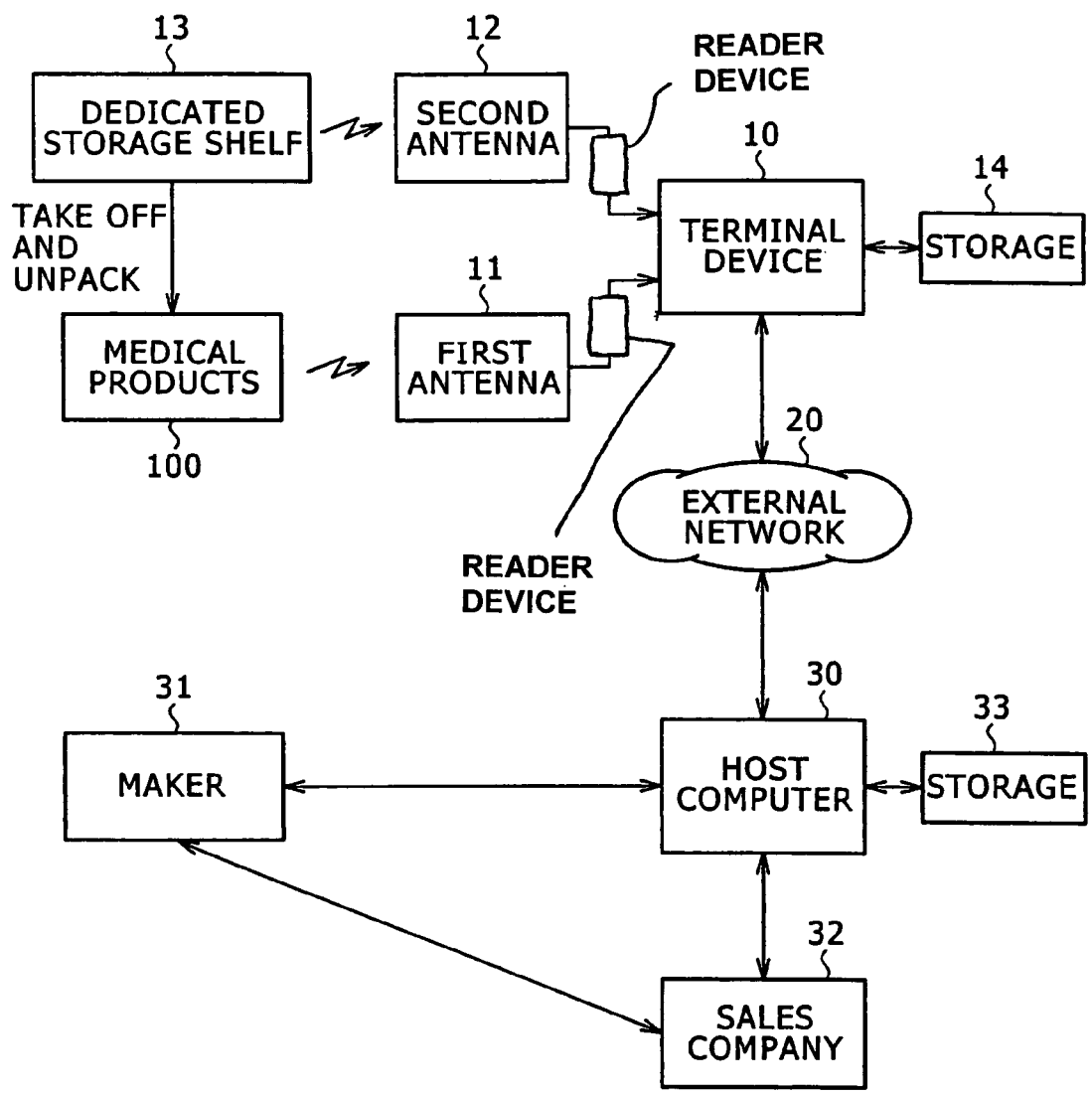
FIG. 5 is a block diagram illustrating an exemplary system configuration practiced as one embodiment of the invention.

The following describes a processing system using the medical product storage pack 100 configured as described above. Referring to FIG. 5, in this embodiment, a data processing terminal 10 (terminal device) based on a computer is arranged in a room (an operating room for example) in which the medical product storage pack 100 is used in a medical center. The terminal 10 is connected, via IC tag readers (reader devices) with a first antenna 11 and a second antenna 12 for wirelessly communicating with the first IC tag 130 and the second IC tag 140 attached to the medical product storage pack 100, thereby reading data from the first IC tag 130 and the second IC tag 140 to create a database (which will be described later) by the terminal 10.

The first antenna 11 is arranged in the vicinity of a desk on which paramedical personnel (e.g., nurses) arrange medical goods for use in surgery, for example in an operating room.

The second antenna 12 is arranged in a medical product storage place (herein referred to as a dedicated storage shelf) 13 arranged in a medical center (in an operating room or in the vicinity thereof, for example), thereby receiving data stored in the second IC tag 140 attached to the medical product storage pack 100 stored on the dedicated storage shelf 13. Therefore, accommodating the medical product storage pack 100 on the dedicated storage shelf 13 allows the acquisition of the information about the types and amounts of stored medical products through the terminal 10. It should be noted that the unused medical goods stored on the dedicated storage shelf 13 in a medical center are stocked on a deposit basis as the property of makers or suppliers in medical center, in general.

The second antenna 12 is operated continuously or at predetermined intervals to get information from the second IC tag 140 every time a new product is stocked on the dedicated storage shelf 13 and to store the obtained information into a database in the terminal 10. The database is stored in a storage section 14 of the terminal 10, for example. Namely, the list of the products stored in the database is matched, from time to time, against the information obtained from the second IC tag 140 of each product detected on the shelf. Hence, when a product is taken from the shelf, it indicates that the signal cannot be obtained from the product stored in the database so far, and so the taking-off of that product from the shelf is obtained as information. When this happens, the information of the second IC tag 140 of the product taken off from the shelf (namely, the product of which signal cannot be detected) is stored in the database as linked with the information indicative of the date and time at which the taking-off occurred.

If the medical product storage pack 100 has been taken off from the dedicated storage shelf 13, the medical product storage pack 100 is put on the above-mentioned desk on which the goods for use in a surgical operation are arranged. Then, when the sterilization pack is opened, the first IC tag 130 contained in the pack is exposed to be ready for signal reception and transmission as described above with reference to FIG. 2. The first antenna 11 is also operated continuously to detect a signal from the first IC tag 130, the detected information being stored in the database of the terminal 10. The database matches the stored information against the take-off information obtained from the second antenna 12 and sets a flag indicating that the medical product storage pack 100 is a used product.

The terminal 10 may be configured as any computer, desktop or mobile, as long as it has a display device. Although not shown, peripheral equipment such as a printer may be connected to the terminal 10.

The terminal 10 arranged in a medical center is configured for connection with an external network 20 such as the Internet for data reception and transmission with the outside. For mating data reception and transmission via the external network 20, a host computer 30 is provided. The updated data of the database is supplied from the terminal 10 in a medical center to the host computer 30 from time to time. The data reception and transmission with the host computer 30 may be made by use of dedicated line or a telephone line connected in a dial-up manner. With reference to FIG. 5, the terminal 10 arranged in, for example, an operating room is directly connected to the external network 20. Alternatively, the data may be transmitted from the terminal 10 to a server arranged in a medical center via a network thereof for making up the data in that server, and then transmitting the resultant data to the external network 20.

The host computer 30 creates a database of the stock of medical goods for each medical center on the basis of the updated data of the database and stores the created database in a storage section 33. The stored data in the storage section 33 is supplied to a terminal device of a medical product maker (manufacturer) 31. On the basis of the supplied data about the types and amounts of medical products used for surgery, the maker 31 transmits data for requesting a supplier for the delivery of medical products and the bills thereof to a terminal device of a supplier 32. The supplier 32 delivers the requested medical products and the bills thereof to the medical center. The host computer 30 is arranged in the maker 31 for example. The maker 31 arranges for the manufacture of the medical products used at a medical center. The delivery of bills may be electronically transmitted to a terminal device of the supply department of a medical center.

The terminal 10 transmits the information about flagged used products to the host computer 30 via the dedicated line or the external network such as the Internet every time the take-off information is obtained or at predetermined intervals (for example once a day). The host computer 30 transmits the supplied information to medical product suppliers or manufacturers along with the information about the name of the medical center and the date of taking-off. At this moment, the host computer may also execute invoice issuance processing for the medical center. Alternatively, the invoice issuance processing may be executed by suppliers or manufacturers.

If the radio range of the first IC tag 130 is long, the first antenna 11 may be arranged anywhere as long as it is indoors. However, if the range is short, the arrangement of the first antenna 11 must be well planned. In the example shown above, a desk is used for a place at which the first antenna 11 is arranged. Alternatively, the first antenna 11 that is connected by wireless LAN for example may be arranged on a cart for carrying medical goods to an operating room or arranged inside for example of a trash box for used packaging materials. In the latter case, the information of the IC tag attached to each discarded packaging material may be read to get data results concerning the medical products used.

It should be noted that if the first antenna 11 does not get unpackaging information within a predetermined period of time (12 hours for example) after the information about the taking-off from the shelf is detected by the second antenna 12 and the taken-off product has not been returned to the shelf, the terminal 10 determines that the product concerned has been lost and notifies the host computer 30 of such matter. Upon reception of this information, the host computer 30 or the supplier or the maker issues a bill for that product.

The terminal 10 is arranged with an input section for entering patient information and the name of the medical procedure (or surgery). Entering the surgery patient information and the name of the surgery that uses a medical product concerned before or after unpackaging the medical product storage pack 100 allows paramedical personnel to use the terminal 10 as a system for recording and managing the medical procedures executed on patients.

Figure 6:
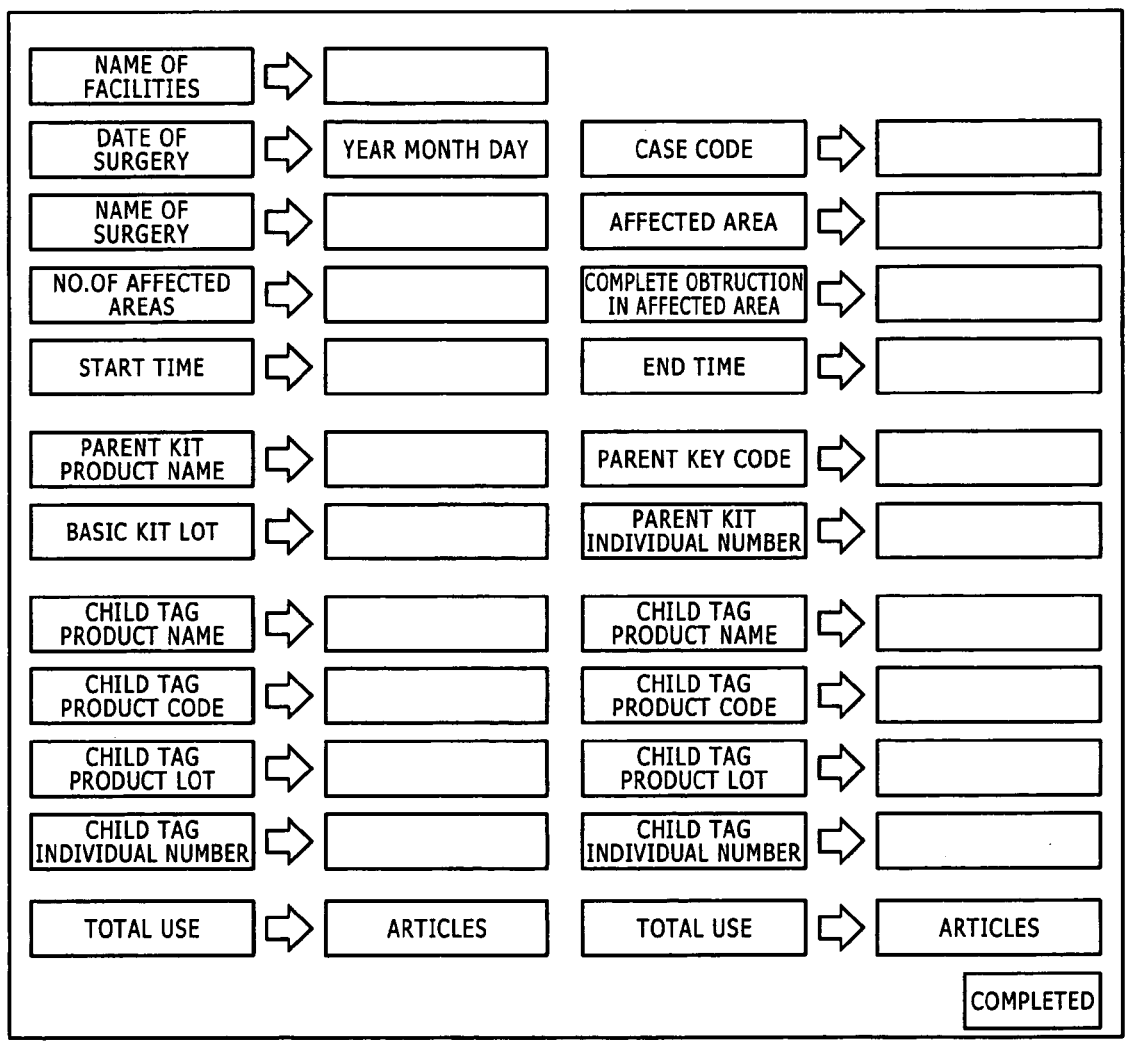
FIG. 6 is a diagram illustrating an exemplary display practiced as one embodiment of the invention.

To be more specific, on the basis of the information stored in a patient medical procedure database, storing patient information and medical procedure (surgery) names, and the information stored in a database storing used products, patient procedure records may be printed or outputted to another system for use. Referring to FIG. 6, there is shown an example of an input screen that is used when creating the patient procedure database. The upper portion of the input screen has boxes to fill in for the name of the facilities, the date of the surgery, the code of the case, the name of the surgery, the affected area, the number of affected areas, the complete obstruction in a blood vessel if any, and the start and end time of a medical check or treatment. Of these pieces of information, the name of the facilities and the date of surgery, for example, may be automatically entered. The lower portion of the input screen has boxes for entering medical products to be used for medical treatment. To be more specific, these boxes are for entering the product name, code number, lot number and individual number of a parent kit (pack) in which medical products to be used for vascular catheterization check or treatment are arranged in a set. Further these boxes are for entering the product names, code numbers, lot numbers and individual numbers of individual products used separately from the parent kit. The individual products include vascular dilatation catheters and stents for example that are not contained in packs, in addition to those products contained in packs, for example.

Of these entries, for products that are taken for use out of the medical product storage pack 100 attached with an IC tag, the types and amount of these products are automatically entered in the corresponding boxes in the screen. It should be noted that it is possible to transmit only the types and amount of used products to the host computer 30, with the above-mentioned detail input data not being transmitted to the host computer 30 to prevent personal information such as patient names from leaking outside.

If the unpackaged product in the present embodiment has been automatically entered as a medical instrument in a detail input screen as shown in FIG. 6 for example, the terminal 10 may determine whether it is proper to use such a medical instrument in the surgery concerned. If the use is found improper, an alert of some form may be issued.

Figure 7:
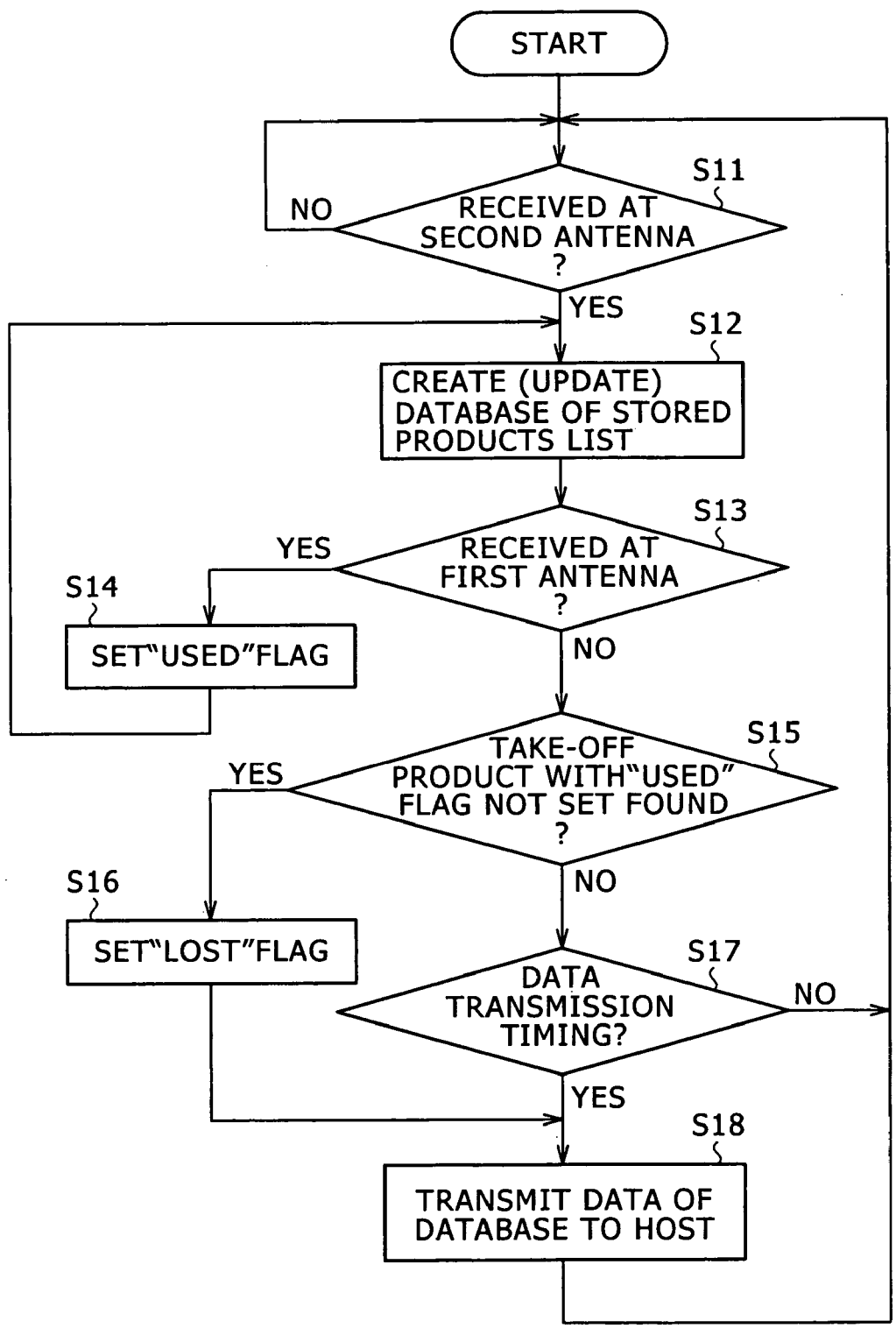
FIG. 7 is a flowchart indicative of exemplary processing to be executed on a terminal device at a medical center practiced as one embodiment of the invention.
Figure 8:
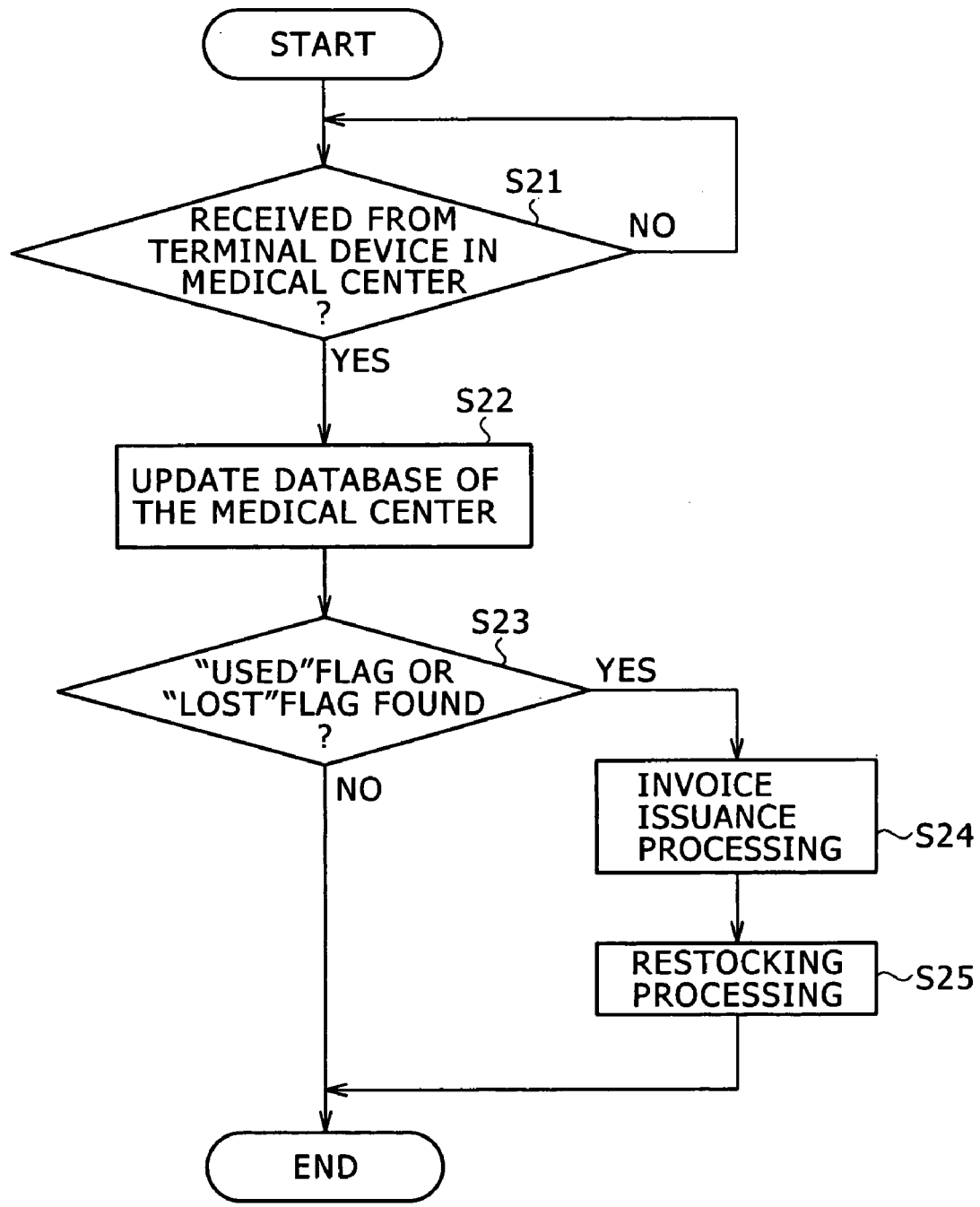
FIG. 8 is a flowchart indicative of exemplary processing to be executed on a host computer practiced as one embodiment of the invention.

The following describes an example of processing of the system of the present embodiment on the side of a medical center and an example on the side of the host computer with reference to the flowcharts shown in FIG. 7 and FIG. 8 respectively.

First, the processing to be executed at the terminal 10 on the side of a medical center will be described with reference to the flowchart shown in FIG. 7. The terminal 10 on the side of a medical center determines whether the second antenna 12 has received data from the second IC tag 140 (step S11). If data is found received from the IC tag, the terminal 10 creates a database of products stored on the dedicated storage shelf 13 on the basis of the received data (step S12). In creating the database, the date and time on which each product was stored on the dedicated storage shelf 13 is also stored in the database.

Next, the terminal 10 determines whether the first antenna 11 has received data from the first IC tag 130 (step S13). If the data is found received, the terminal 10 sets flag "USED" to the product having a serial number indicated by the received data in the database (step S14). Then, back to step S12, the terminal 10 updates the database. At this moment, the date of reception at the first antenna 11 for example (namely, the date on which the product was used) is also stored.

If the first antenna 11 has received no data from the first IC tag 130 after the creation (or updating) of the database, the terminal 10 determines whether there is any product among the medical products stored in the database of which no data can be received from the second IC tag 140 by the second antenna 12 with flag "USED" not set (namely, any product in the database not found without any signs of use) (step S15). Here, this determination is made if there is no sign of use a predetermined period of time (12 hours for example) after the product was taken off from the dedicated storage shelf 13 for example. If such a product is found, the terminal 10 sets flag "LOST" to the product having the corresponding serial number in the database (step S16).

If no lost product is found in step S15, then the terminal 10 determines whether a predetermined data transmission timing has come (step S17). If the predetermined data transmission timing is found to not have been reached, the terminal 10 returns to the reception processing of the second antenna 12 and the database update processing on the basis of the received data in step S11. It should be noted that in setting the data transmission timing at certain time intervals, the terminal 10 may return to the processing of step S11 also when there is no change in the data in the database from the data transmitted last.

If the data transmission timing is found to have been reached in step S17 and if flag "LOST" was set in step S16, the terminal 10 transmits the data in the database of the terminal 10 to the host computer 30 (step S18), upon which the terminal 10 returns to the processing of step S11.

The following describes an example of processing by the host computer 30 with reference to the flowchart shown in FIG. 8. The host computer 30 determines whether data has come (or has been received) from the medical center's terminal 10 managed by the host computer 30 (step S21). If the data is found to have been received, the host computer 30 uses the received data to update a database storing the corresponding medical center's product stock and use results (step S22). Next, the host computer 30 determines whether the update data includes data to which the flag "USED" and/or the flag "LOST" is set (step S23). If the data to which the flag "USED" and/or the flag "LOST" is found, the host computer 30 executes invoice issuance processing for each product to which the flag "USED" is set and/or each product to which the flag "LOST" is set (step S24). In addition, the host computer 30 executes restocking processing for replenishing the stock of the medical center for each product to which the flag "USED" is set and/or each product to which the flag "LOST" is set (step S25). These invoice issuance processing and restocking processing are executed via a supplier for example.

Thus, on the basis of the data received from IC tags on the side of medical centers, a database of unused stock is created and the created database is sent to the host side, thereby automating medical product stock management and invoice issuance processing. Therefore, unlike related-art technologies that require human interventions such as passing medical products through a dedicated information reading gate every time they are used, the system practiced as one embodiment of the invention is capable of reliably managing the use of medical products.

In the example described so far, an IC tag is arranged between electromagnetic shield members such that the signal transmission is blocked in the sterilized state and enabled when the package is opened to so that the sterilized state no longer exists. However, an alternative configuration may be used. For example, the transmission/reception antenna of each IC tag may be physically short-circuited in the packaged state, thereby disabling the signal transmission from the IC tag.

Figure 9:
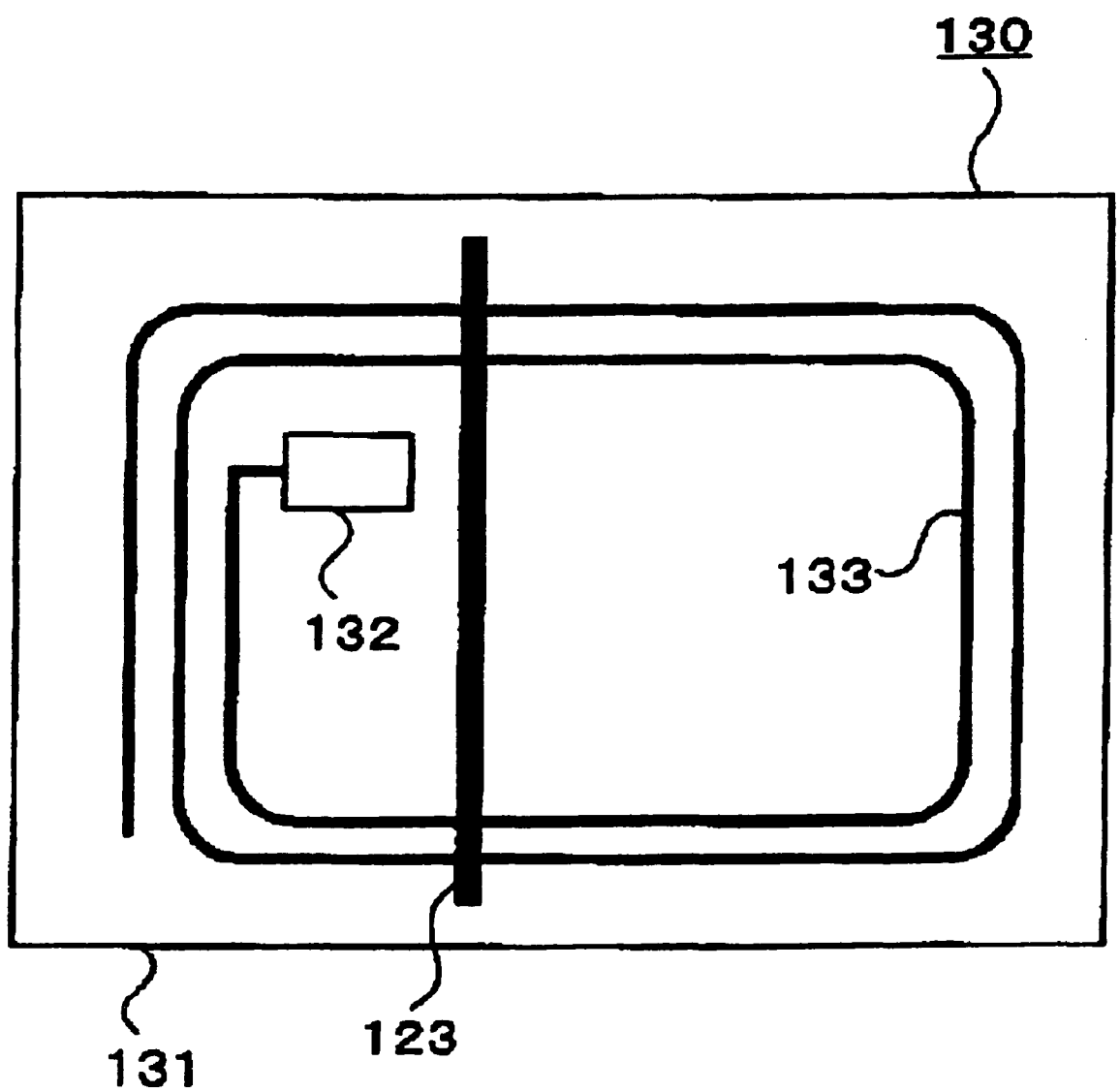
FIG. 9 is a top view illustrating an example in which an IC tag practiced as another embodiment of the invention is short-circuited.

More specifically, as shown by way of example in FIG. 9, an IC chip 132 can be arranged on a base 131 as the first IC tag 130 and a coil antenna 133 connected to the IC chip 132 can be arranged on the base 131. With the first IC tag 130 having this configuration, a short-circuit part 123 made of an electrically conductive member is brought into contact with the antenna 133 with the medical product storage pack 100 in the packaged state, thereby disabling the electromagnetic wave reception by the antenna 133. Because the IC tag obtains signal transmission energy (or electrical power) by receiving electromagnetic waves such as an RF signal at the antenna 133, the signal transmission from the first IC tag 130 is disabled.

The short-circuit part 123 is adhesively attached to release coated paper on the base so that the short-circuit part 123 may be detached from the base 131 by pulling a pull end of the short-circuit part 123 in the same manner as shown in FIGS. 1-4. In this configuration, the opening of the medical product storage pack 100 removes the short-circuit part 123 from the IC tag to make the antenna of the IC tag regain its full length, thereby making the IC tag ready for receiving and transmitting electromagnetic waves. Also, it is possible that the IC tag is adhesively attached to the release coated paper of the pull end side and the short-circuit part is arranged on the lower side. In this configuration, when the IC tag is peeled off the release coated paper by pulling the pull end section, the short-circuit part stays unremoved. The electrically conductive member for forming the short-circuit part may be a metal such as copper or aluminum or an electrically conductive ink.

The above-mentioned terminals arranged in medical centers and the host computer may be realized by installing the software programs for executing the processing of the above-mentioned embodiment into general-purpose computers, allowing the building of the above-mentioned system according to one embodiment of the invention with ease. The software programs for this purpose may be provided in a variety of recording media or by downloading through communication means such as the Internet.

In the above-mentioned embodiment, the terminals in medical centers and the host computer are interconnected by some communication means for automatic data transmission and reception. Alternatively, the personnel of medical product suppliers may go to medical centers at regular time intervals (once every several days, for example) with a portable data processing device (a laptop computer for example), connect this portable device to the terminal of each medical center, read the data therefrom to record the data to the portable device, bring the portable device back to the supplier's office, and transmit the data thus brought to the host computer from the supplier's office, for example.

In the above-mentioned embodiment, such medical products for use in surgery as vascular catheters and accessories thereof are mentioned as examples of medical products contained in a pack with an IC tag in the sterilized state. The present embodiment of the invention is also applicable to the packaging of other medical products (medical instruments, drugs and medicines, and so on) if these medical products are encapsulated for storage in the packaging in the sterilized state.

In the above-mentioned embodiment, both the first IC tag that cannot be read in the packaged state and the second IC tag that can be read normally are attached to each medical product storage pack. As an alternative, the second IC tag is not attached to the medical product storage pack, in which the stock management on the stock shelf is executed by another method using no IC tag, and only the first tag that cannot be read in the packaged state is attached to the medical product storage pack, thereby executing only the confirmation of medical products for use in surgery.

While preferred embodiments of the present invention have been described using specific terms, such description is for illustrative purpose only, and it is to be understood that changes and variations may be made, and equivalents employed, without departing from the spirit and scope of the invention as defined by the claims.

What is claimed is:

1. A medical product storage pack comprising a package, a medical product encapsulated in a sterilized environment in the package, and a first IC tag arranged at the package such that at least one of signal transmission and signal reception by said first IC tag is disabled, and such that said at least one of signal reception and signal transmission by said first IC tag is enabled upon opening said package to permit removal of said medical product from said package, wherein said first IC tag, prior to the opening of the package, is sandwiched in a space between electromagnetic wave shield sheets that are integrally attached to portions of said package such that said electromagnetic wave shield sheets are separated away from each other when said package is opened;

wherein the space in which said first IC tag is arranged is separated from a storage section for storing the medical product, so the electromagnetic shield sheets cover the space in which said first IC tag is arranged, and do not cover the storage section;

wherein the package further comprises a pull section for opening of the package, the space in which the pull section is arranged being located near the IC tag rather than the storage section such that pulling the pull section firstly exposes said entire first IC tag and secondly unpackages the storage section.

2. The medical product storage pack according to claim 1, wherein said first IC tag comprises an antenna that is at least one of a signal transmission antenna and a signal reception antenna, and an electrically conductive strip adhesively secured to said antenna, the electrically conductive strip being peeled off from said antenna when said package is opened.

3. The medical product storage pack according to claim 2, wherein said shielded space and said storage space are both exposed when said package is opened.

4. The medical product storage pack according to claim 3, further comprising a second IC tag enabled for at least one of signal transmission and signal reception when said medical product is encapsulated in the sterilized environment.

5. The medical product storage pack according to claim 1, wherein said shielded space and said storage space are both exposed when said package is opened.

6. The medical product storage pack according to claim 5, further comprising a second IC tag enabled for at least one of signal transmission and signal reception when said medical product is encapsulated in the sterilized environment.

7. The medical product storage pack according to claim 1, and further comprising a second IC tag enabled for at least one of signal transmission and signal reception when said medical product is encapsulated in the sterilized environment.

8. The medical product storage pack according to claim 1, wherein, when opening the package, said first IC tag is exposed prior to opening of the storage section.

9. A medical product storage pack comprising:
a closed package possessing an enclosed first space in which is located a medical product under sterilized conditions, the closed package being openable so that the first space is no longer under sterilized conditions to permit removal of the medical product from the package;
a first IC tag arranged in a second space formed in the package; and
means for disabling at least one of signal transmission and signal reception by said first IC tag when the package is closed and for enabling at least one of the signal reception and the signal transmission by said first IC tag when the package is opened so that the first space is no longer under sterilized conditions;
wherein said means comprises electromagnetic wave shield sheets that are integrally attached to portions of said package to form said second space and sandwich said first IC tag therebetween, said electromagnetic wave shield sheets being separated away from each other when said package is opened;
wherein the second space in which said first IC tag is arranged is separated from said first space, so the electromagnetic shield sheets cover the first space, and do not cover the second space;
wherein the package further comprises a pull section for opening of the package, the space in which the pull section is arranged being located near said first IC tag rather than the storage section such that pulling the pull section firstly exposes said entire IC tag and secondly unpackages the storage section.

10. The medical product storage pack according to claim 9, wherein said first and second spaces are both exposed when said package is opened.

11. The medical product storage pack according to claim 9, wherein said first space is exposed prior to second space being exposed when said package is opened.

* * * * *